(12) United States Patent
Kang et al.

(10) Patent No.: US 9,499,488 B2
(45) Date of Patent: Nov. 22, 2016

(54) VITAMIN D RECEPTOR AGONISTS AND USES THEREOF

(75) Inventors: Peter M. Kang, Lexington, MA (US); S. Ananth Karumanchi, Chestnut Hill, MA (US); Santosh Khedkar, Somerville, MA (US); Alan Rigby, Newton, MA (US); Ravi I. Thadhani, Boston, MA (US)

(73) Assignees: Beth Israel Deaconess Medical Center, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/232,196

(22) PCT Filed: Jul. 11, 2012

(86) PCT No.: PCT/US2012/046154
§ 371 (c)(1),
(2), (4) Date: Aug. 29, 2014

(87) PCT Pub. No.: WO2013/009799
PCT Pub. Date: Jan. 17, 2013

(65) Prior Publication Data
US 2014/0378507 A1 Dec. 25, 2014

Related U.S. Application Data

(60) Provisional application No. 61/506,423, filed on Jul. 11, 2011.

(51) Int. Cl.
| | |
|---|---|
| *A01N 43/42* | (2006.01) |
| *A61K 31/47* | (2006.01) |
| *C07D 215/54* | (2006.01) |
| *A61K 31/63* | (2006.01) |
| *C07C 311/46* | (2006.01) |
| *C07C 311/21* | (2006.01) |

(52) U.S. Cl.
CPC ........... *C07D 215/54* (2013.01); *A61K 31/47* (2013.01); *A61K 31/63* (2013.01); *C07C 311/21* (2013.01); *C07C 311/46* (2013.01)

(58) Field of Classification Search
None
See application file for complete search history.

(56) References Cited

U.S. PATENT DOCUMENTS

| | | | |
|---|---|---|---|
| 2005/0137190 A1 | 6/2005 | Gonzalez et al. | |
| 2006/0135403 A1* | 6/2006 | Gervais | A61K 31/185 424/400 |
| 2007/0112015 A1* | 5/2007 | Hurt et al. | 514/264.1 |
| 2010/0119599 A1 | 5/2010 | Mullan et al. | |
| 2011/0015201 A1 | 1/2011 | Chen et al. | |

FOREIGN PATENT DOCUMENTS

WO    WO 2008070875 A2 *   6/2008   ............. A61K 31/47

OTHER PUBLICATIONS

STN CAS RN: 2128-19-0 (entered STN Nov. 16, 1984).*
Banjeree et al., "Vitamin D and Alzheimer's Disease: Neurocognition to Therapeutics," International Journal of Alzheimer's Diseasevol. 2015 (2015), Article ID 192747, 11 pages.*
International Preliminary Report on Patentability and Written Opinion for International Application No. PCT/US2012/046154, issued Jan. 14, 2014 (7 pages).
International Search Report for International Application No. PCT/US2012/046154, mailed Sep. 18, 2012 (3 pages).
Linden et al., "Cocrystals of diastereoisomers of 1,4-dihydropyridine derivatives." Act Crystallogr C. 62(Pt 4):o227-30 (2006).
McKay et al., "Analogs of methyllycaconitine as novel noncompetitive inhibitors of nicotinic receptors: pharmacological characterization, computational modeling, and pharmacophore development." Mol Pharmacol. 71(5):1288-97 (2007).
Aoki et al., "Direct activation of mitochondrial apoptosis machinery by c-Jun N-terminal kinase in adult cardiac myocytes," J Biol Chem. 277(12):10244-50 (2002).
Cantorna, "Vitamin D and its role in immunology: multiple sclerosis, and inflammatory bowel disease," Prog Biophys Mol Biol. 92(1):60-4 (2006).
Choi et al., "Therapeutic applications for novel non-hypercalcemic vitamin D receptor ligands," Expert Opin Ther Pat. 19(5):593-606 (2009).
Xiang et al., "Catalytic degradation of vitamin D up-regulated protein 1 mRNA enhances cardiomyocyte survival and prevents left ventricular remodeling after myocardial ischemia," J Biol Chem. 280(47):39394-402 (2005).
Zhu et al., "Calcium and 1 alpha,25-dihydroxyvitamin D3 target the TNF-alpha pathway to suppress experimental inflammatory bowel disease," Eur J Immunol. 35(1):217-24 (2005).

* cited by examiner

*Primary Examiner* — Jared D Barsky
(74) *Attorney, Agent, or Firm* — Kristina Bieker-Brady; Clark & Elbing LLP

(57) ABSTRACT

This invention features vitamin D receptor agonists, and their use in treating bone disorders, cardiovascular disease, hyperparathyroidism, immune disorders, proliferative disease, renal disease, and thrombosis.

3 Claims, 5 Drawing Sheets

Figure 1. Effect of compound A in adult cardiomyocyte culture after PE-induced hypertrophy. ANP=atrial natriuretic peptide, GAPDH=Glyceraldehyde 3-phosphate dehydrogenase, PE=phenylephrine, PC=paricalcitol, A=compound A. *=p<0.05 vs PE. N=4.

VITAMIN D RECEPTOR AGONISTS AND USES THEREOF

CROSS-REFERENCE TO RELATED APPLICATIONS

This application is the U.S. National Stage of International Application No. PCT/US2012/046154, filed Jul. 11, 2012, which claims benefit of U.S. Provisional Application No. 61/506,423, filed Jul. 11, 2011, which is hereby incorporated by reference.

BACKGROUND OF THE INVENTION

This invention relates to the field of vitamin D receptor agonists. The agonists can be used as drugs to treat a variety of diseases, including, but not limited to, bone disorders, cardiovascular disease, hyperparathyroidism, immune disorders, proliferative diseases, renal disease, and thrombosis.

Vitamin D3 is a precursor to the functionally active hormone, 1,25-dihydroxyvitamin D3. Vitamin D3 is made from 7-dehydrocholesterol in the skin after exposure to ultraviolet light, modified by vitamin D3-25-hydroxylase in the liver, and then by 25-hydroxyvitamin D3-1α-hydroxylase in the kidney to form the active hormone, 1,25-dihydroxyvitamin D3 (calcitriol, commercially available under the brand name CALCIJEX®). Calcitriol functions by binding to the Vitamin D receptor (VDR), a nuclear receptor. The binding of calcitriol to the VDR activates the receptor to recruit cofactors to form a complex that binds to vitamin D response elements in the promoter region of target genes to regulate gene transcription.

Calcitriol plays a biochemical role in mineral homeostasis, which covers regulation of parathyroid hormone (PTH), intestinal calcium and phosphate absorption, and bone metabolism. Through the coordinated functions of PTH and calcitriol, the homeostasis of calcium and phosphorous is maintained.

VDR is widely distributed in organs and tissues throughout the body and is implicated in numerous disease states (e.g., cardiovascular diseases, immune disorders, oncology-related thrombosis, etc.).

Analogs of calcitriol have been developed, some having reduced hypercalcemic effect, and several analogs such as paricalcitol (ZEMPLAR®) and doxercalciferol (HECTOROL®) are currently on the market for the treatment of hyperparathyroidism secondary to chronic kidney disease. In addition, a few VDR modulators are marketed for the treatment of psoriasis and osteoporosis.

However, at least some VDR modulators, especially at higher doses, can cause hypercalcemia, which has been linked to vascular calcification, myocardial infarction, heart failure, cardiomyopathy, and stroke. As a result of such side effects and related adverse events, the use of VDR modulators for the treatment of, for example, cardiovascular disease and psoriasis may be limited for safety reasons.

Given the potential limitation of compounds that do result in hypercalcemia it would be advantageous to develop vitamin D receptor modulators that have beneficial therapeutic effects, while having limited effect on increasing serum calcium levels, essentially increasing the therapeutic window for such drugs, and expanding use of VDR modulator therapy.

SUMMARY OF THE INVENTION

We have discovered chemical chemotypes which act as vitamin D receptor agonists. The agonists can be used as drugs to treat a variety of diseases, including, but not limited to, bone disorders, cardiovascular disease, hyperparathyroidism, immune disorders, proliferative diseases, renal disease, and thrombosis.

The invention features a method for treating a vitamin D receptor-mediated condition in a subject by administering to the subject in an amount sufficient to treat the condition a compound of formula (I), or a pharmaceutically acceptable salt thereof:

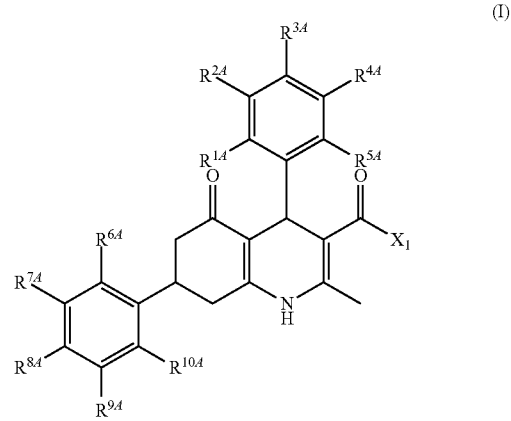

(I)

In formula (I), each of $R^{1A}$, $R^{2A}$, $R^{3A}$, $R^{4A}$, $R^{5A}$, $R^{6A}$, $R^{7A}$, $R^{8A}$, $R^{9A}$, and $R^{10A}$ is, independently, selected from H, halide, nitro, $CF_3$, OH, $OR^{11A}$, $C_{1-4}$ alkyl, $C_{1-4}$ heteroalkyl, $C_{2-4}$ alkenyl, and $C_{2-4}$ alkynyl; $X_1$ is $NHR^{12A}$, $OR^{12A}$, or $SR^{12A}$; $R^{11A}$ is selected from $C_{1-4}$ alkyl, $C_{2-4}$ alkenyl, and $C_{2-4}$ alkynyl; and $R^{12A}$ is selected from $C_{1-6}$ alkyl, $C_{1-6}$ heteroalkyl, $C_{2-6}$ alkenyl, $C_{2-6}$ alkynyl, $C_{6-12}$ alkaryl, and $C_{6-12}$ heteroalkaryl. In particular embodiments, the compound of formula (I) is administered as a substantially pure composition including a compound of any of formulas (Ia)-I(d):

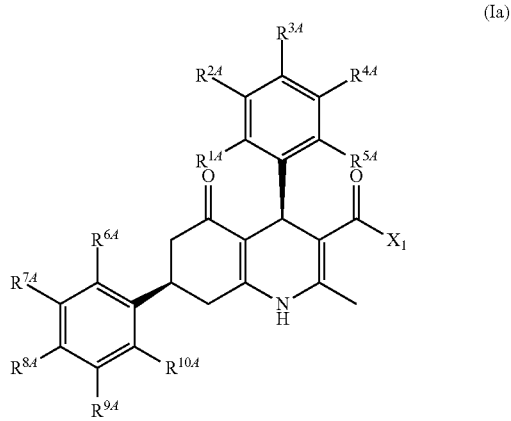

(Ia)

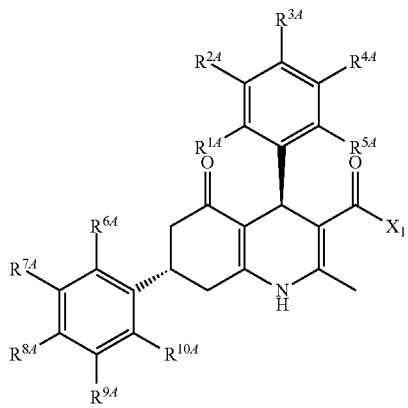
(Ib)

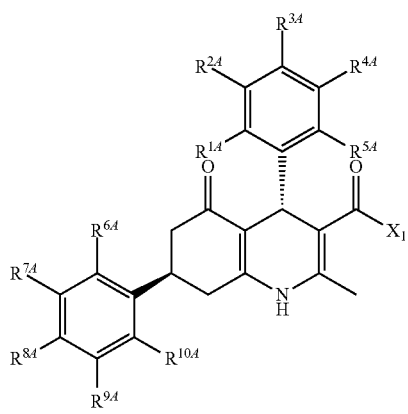
(Ic)

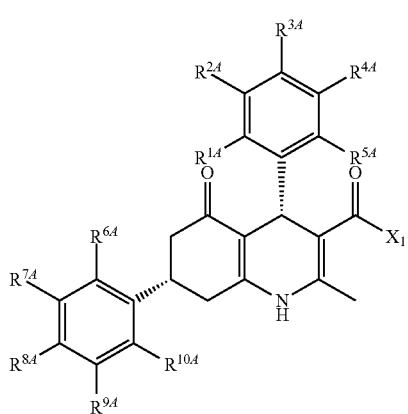
(Id)

In formulas (Ia)-I(d), $R^{1A}$, $R^{2A}$, $R^{3A}$, $R^{4A}$, $R^{5A}$, $R^{6A}$, $R^{7A}$, $R^{8A}$, $R^{9A}$, $R^{10A}$ and $X_1$ are as defined in formula (I).

In a related aspect, the invention features a method for treating a vitamin D receptor-mediated condition in a subject by administering to the subject in an amount sufficient to treat the condition a compound of formula (II), or a pharmaceutically acceptable salt thereof:

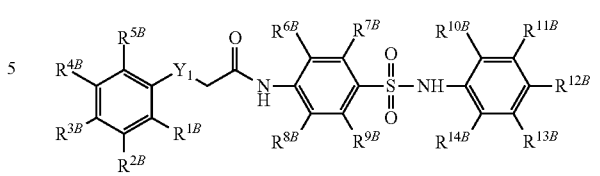
(II)

In formula (II), each of $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{13B}$, and $R^{14B}$ is, independently, selected from H, halide, nitro, OH, $OR^{15B}$, $C_{1-4}$ haloalkyl, $C_{1-4}$ alkyl, $C_{1-4}$ heteroalkyl, $C_{2-4}$ alkenyl, and $C_{2-4}$ alkynyl; $Y_1$ is O or S; and $R^{15B}$ is selected from $C_{1-4}$ alkyl, $C_{2-4}$ alkenyl, and $C_{2-4}$ alkynyl.

In any of the above methods, the vitamin D receptor-mediated condition can be selected from bone disorders (e.g., osteoporosis, osteomalacia, or osteodystrophy), cardiovascular disease (e.g., thrombus formation, myocardial hypertrophy, or hypertension), hyperparathyroidism, immune disorders, proliferative diseases (e.g., cancer, prostatic hyperplasia, psoriasis, and dandruff), renal disease, thrombosis, and any other conditions described herein. In certain embodiments, the vitamin D receptor-mediated condition is renal disease or secondary hyperparathyroidism associated with chronic kidney disease. In other embodiments, the vitamin D receptor-mediated condition is an immune disorder, such as a nondermal inflammatory disorder (e.g., gout, arthritis, osteoarthritis, rheumatoid arthritis, Crohn's disease, ulcerative colitis, ileitis, ileocolitis, collagenous colitis, lymphocytic colitis, ischaemic colitis, diversion colitis, Behçet's syndrome, indeterminate colitis, Crohn's colitis, Crohn's enteritis, Crohn's terminal ileitis, Crohn's entero-colitis, ileo-colitis, asthma, chronic obstructive pulmonary disease, bronchitis, rhinitis, sinusitis, rhinosinusitis, uveitis, anterior uveitis, intermediate uveitis, posterior uveitis, panuveitis, vernal keratoconjunctivitis, atopic keratoconjunctivitis, iritis, or giant papillary conjunctivitis), a nonproliferative dermal inflammatory disorder (e.g., acne, erythema multiforme, rash, and rosacea), an allergic reaction (e.g., asthma, graft versus host disease, contact dermatitis, urticaria, or allergic rhinitis), or a proliferative dermal inflammatory disorder (e.g., psoriasis and eczema).

The invention features a pharmaceutical composition including a compound of formula (I), or a pharmaceutically acceptable salt thereof, and a pharmaceutically acceptable excipient:

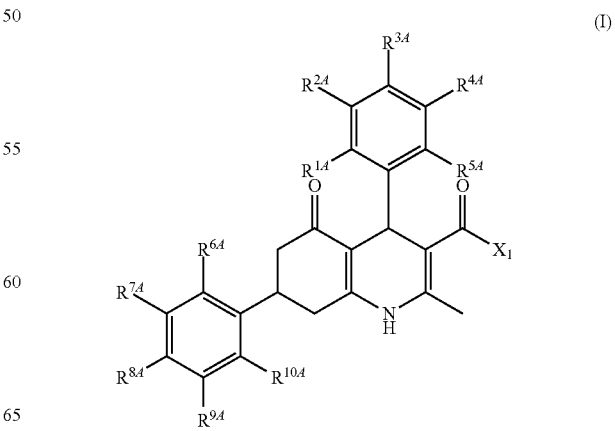
(I)

In formula (I), each of $R^{1A}$, $R^{2A}$, $R^{3A}$, $R^{4A}$, $R^{5A}$, $R^{6A}$, $R^{7A}$, $R^{8A}$, $R^{9A}$, and $R^{10A}$ is, independently, selected from H, halide, nitro, $CF_3$, OH, $OR^{11A}$, $C_{1-4}$ alkyl, $C_{1-4}$ heteroalkyl, $C_{2-4}$ alkenyl, and $C_{2-4}$ alkynyl; $X_1$ is $NHR^{12A}$, $OR^{12A}$, or $SR^{12A}$; $R^{11A}$ is selected from $C_{1-4}$ alkyl, $C_{2-4}$ alkenyl, and $C_{2-4}$ alkynyl; and $R^{12A}$ is selected from $C_{1-6}$ alkyl, $C_{1-6}$ heteroalkyl, $C_{2-6}$ alkenyl, $C_{2-6}$ alkynyl, $C_{6-12}$ alkaryl, and $C_{6-12}$ heteroalkaryl. In particular embodiments, the pharmaceutical composition is a substantially pure pharmaceutical composition including a compound of any of formulas (Ia)-I(d):

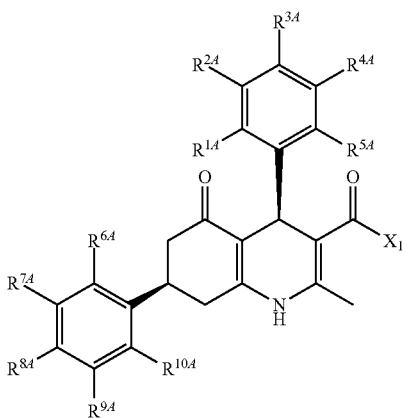

(Ia)

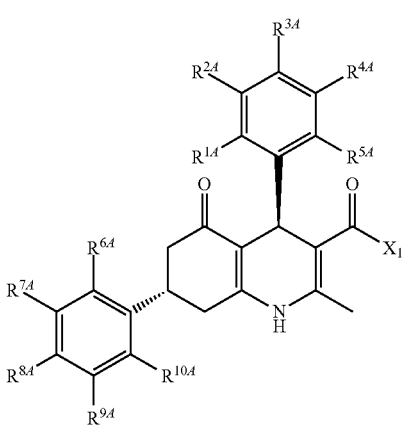

(Ib)

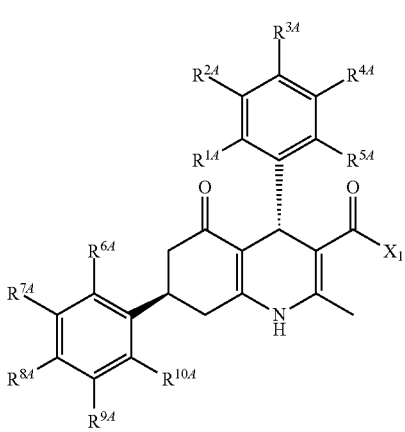

(Ic)

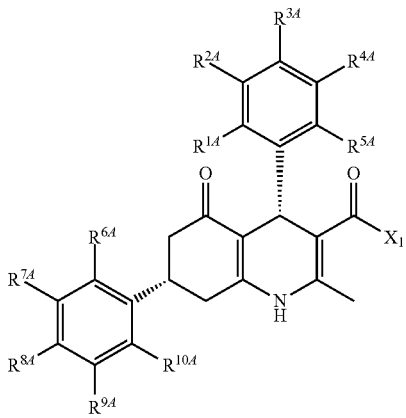

(Id)

In formulas (Ia)-I(d), $R^{1A}$, $R^{2A}$, $R^{3A}$, $R^{4A}$, $R^{5A}$, $R^{6A}$, $R^{7A}$, $R^{8A}$, $R^{9A}$, $R^{10A}$ and $X_1$ are as defined in formula (I). The pharmaceutical composition can be formulated for topical administration, oral administration, intravenous administration, or any other route of administration described herein. For example, the pharmaceutical composition can be a unit dosage form including from 0.02 μg to 50 μg (e.g., from 0.02 μg to 0.1 μg, 0.05 μg to 0.5 μg, 0.1 μg to 5 μg, 0.5 μg to 7 μg, 0.1 μg to 1 μg, 1 μg to 5 μg, 2 μg to 10 μg, 7 μg to 12 μg, or from 10 μg to 50 μg) of the compound of formula (I), or a pharmaceutically acceptable salt thereof. The pharmaceutical composition can be formulated for topical administration (e.g., as a cream, lotion, spray, or ointment) and include from 0.00005% to 5% (w/w) (e.g., from 0.00005% to 5%, 0.00005% to 0.0001%, 0.0001% to 0.001%, 0.001% to 0.01%, 0.01% to 0.1%, 0.1% to 0.5%, 0.25% to 1.0%, or from 0.5% to 5% (w/w)) of the compound of formula (I), or a pharmaceutically acceptable salt thereof.

The invention further features a pharmaceutical composition including a compound of formula (II), or a pharmaceutically acceptable salt thereof, and a pharmaceutically acceptable excipient:

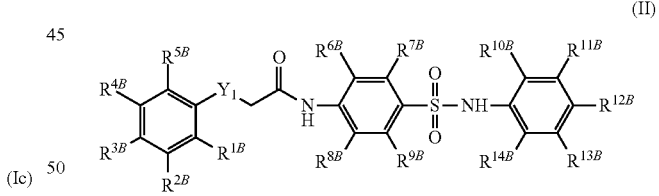

(II)

In formula (II), each of $R^{1B}$, $R^{2B}$, $R^{3B}$, $R^{4B}$, $R^{5B}$, $R^{6B}$, $R^{7B}$, $R^{8B}$, $R^{9B}$, $R^{10B}$, $R^{11B}$, $R^{12B}$, $R^{13B}$, and $R^{14B}$ is, independently, selected from H, halide, nitro, OH, $OR^{15B}$, $C_{1-4}$ haloalkyl, $C_{1-4}$ alkyl, $C_{1-4}$ heteroalkyl, $C_{2-4}$ alkenyl, and $C_{2-4}$ alkynyl; $Y_1$ is O or S; and $R^{15B}$ is selected from $C_{1-4}$ alkyl, $C_{2-4}$ alkenyl, and $C_{2-4}$ alkynyl. The pharmaceutical composition can be formulated for topical administration, oral administration, intravenous administration, or any other route of administration described herein. For example, the pharmaceutical composition can be a unit dosage form including from 0.02 μg to 50 μg (e.g., from 0.02 μg to 0.1 μg, 0.05 μg to 0.5 μg, 0.1 μg to 5 μg, 0.5 μg to 7 μg, 0.1 μg to 1 μg, 1 μg to 5 μg, 2 μg to 10 μg, 7 μg to 12 μg, or from 10 μg to 50 μg) of the compound of formula (II), or a pharmaceutically acceptable salt thereof. The pharmaceutical composition can be formulated for topical administration (e.g., as a cream, lotion, spray, or ointment) and include from 0.00005% to 5% (w/w) (e.g., from 0.00005% to 5%, 0.00005% to 0.0001%, 0.0001% to 0.001%, 0.001% to 0.01%, 0.01% to 0.1%, 0.1% to 0.5%, 0.25% to 1.0%, or from 0.5% to 5% (w/w)) of the compound of formula (II), or a pharmaceutically acceptable salt thereof.

In particular embodiments of the above methods and compositions including a compound of formula (I), $R^{1A}$ is selected from H, halide, $OCH_3$, and $CH_3$; $R^{2A}$ is selected from H, OH, $OCH_3$, and $CH_2CH_3$; $R^{3A}$ is selected from H, halide, OH, $OCH_3$, $CH_3$, and $CH_2CH_3$; $R^{8A}$ is selected from H, halide, and $OCH_3$; $R^{10A}$ selected from H and $OCH_3$; and/or each of $R^{4A}$, $R^{5A}$, $R^{6A}$, $R^{7A}$, and $R^{9A}$ is H. In certain embodiments, $X_1$ is $OR^{12A}$; and $R^{12A}$ is selected from $CH_2CH_3$, $CH_2CH_2OCH_2CH_3$, $CH_2CH_2SCH_2CH_3$, $CH_2CH_2OPh$, and $CH_2CH_2SPh$. In any of the above methods and compositions, the compound of formula (I) can be any of compounds 1-17 described herein, or a pharmaceutically acceptable salt thereof.

In particular embodiments of the above methods and compositions including a compound of formula (II), $R^{3B}$ is selected from H, halide, $CH_3$, and $CH_2CH_3$; $R^{4B}$ is selected from H and $CH_3$; $R^{5B}$ is selected from H, halide, and $CH_3$; each of $R^{10B}$, $R^{11B}$, $R^{12B}$, $R^{13B}$, and $R^{14B}$ is, independently, selected from H, $OCH_3$, and $CH_3$; and/or each of $R^{1B}$, $R^{2B}$, $R^{6B}$, $R^{7B}$, $R^{8B}$, and $R^{9B}$ is H. In certain embodiments, $Y_1$ is O. In any of the above methods and compositions, the compound of formula (II) can be any of compounds 18-24 described herein, or a pharmaceutically acceptable salt thereof.

Pharmaceutical formulations containing a compound of the invention, if not specified otherwise, can include isomers such as diastereomers and enantiomers, mixtures of isomers, including racemic mixtures, and salts thereof.

The term "acne" is a general term to denote inflammatory disorders of the pilosebaceous unit. Acne is a group of disorders whose initial pathology is the comedo and includes acne vulgaris (common acne), neonatal acne, infantile acne, and pomade acne.

By "effective" amount is meant the amount of a compound of the invention required to treat or prevent a vitamin D receptor-mediated condition. Vitamin D receptor-mediated conditions include those conditions in which treatment with a vitamin D modulator may provide synergy, additivity, and/or superiority to existing treatment regimens. The effective amount of a compound of the invention used to practice the invention for therapeutic or prophylactic treatment of vitamin D receptor-mediated conditions varies depending upon the condition, the route of administration, the age, body weight, and general health of the subject. Ultimately, the attending physician will decide the appropriate dose as well as dosing regimen. Such amount is referred to as an "effective" amount.

By "musculoskeletal disorder" is meant an immune system-related disorder of the muscles, ligaments, bones, joints, cartilage, or other connective tissue. Among the most commonly-occurring musculoskeletal disorders are various forms of arthritis, e.g., osteoarthritis, rheumatoid arthritis, juvenile rheumatoid arthritis, and gout.

The term "nondermal inflammatory disorder" refers to an autoimmune condition (e.g., musculoskeletal disorders, autoimmune diseases of the GI tract, and ocular autoimmune diseases), but specifically excludes inflammatory dermatoses. Nondermal inflammatory disorders include, without limitation, musculoskeletal disorders, such as arthritis, osteoarthritis, and rheumatoid arthritis; inflammatory bowel diseases, such as Crohn's disease, ulcerative colitis, ileitis, ileocolitis, collagenous colitis, lymphocytic colitis, ischaemic colitis, diversion colitis, Behçet's syndrome, indeterminate colitis, Crohn's colitis, Crohn's enteritis, Crohn's terminal ileitis, Crohn's entero-colitis, and ileo-colitis; inflammatory respiratory conditions, such as asthma, chronic obstructive pulmonary disease, bronchitis, rhinitis, sinusitis, and rhinosinusitis; and inflammatory ocular conditions, such as uveitis, anterior uveitis, intermediate uveitis, posterior uveitis, panuveitis, vernal keratoconjunctivitis, atopic keratoconjunctivitis, iritis, and giant papillary conjunctivitis, By "nonproliferative dermal inflammatory disorders" or "nonproliferative inflammatory dermatoses" is meant an inflammatory disorder of the skin which is not also a proliferative skin disease. Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function. Nonproliferative dermal inflammatory disorders include acne, erythema multiforme, rash, and rosacea.

By "pharmaceutical composition" is meant a composition containing a compound of the invention, formulated with a pharmaceutically acceptable excipient, and approved for manufacture or sale by a regulatory agency (e.g., the FDA) as part of a therapeutic regimen for the treatment or prevention of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

By "proliferative skin disease" is meant a benign or malignant disease that is characterized by accelerated cell division in the epidermis or dermis. Examples of proliferative skin diseases are psoriasis, eczema, dandruff, actinic keratosis, basal and squamous cell carcinomas of the skin, lamellar ichthyosis, epidermolytic hyperkeratosis, mycosis fungoides, lichen planus, and other skin diseases characterized by rapid proliferation of skin cells.

The term "rosacea" refers to a chronic inflammatory skin disorder characterized by prominent cutaneous blood vessels, erythema, papules, and pustules primarily in the central areas of the face. Tissue hypertrophy, particularly of the nose, may result. Rarely, rosacea occurs on the trunk and extremities. The cause is unknown, but the disease is most common in persons with a fair complexion.

As used herein, "substantially pure" refers to compositions containing a compound of the invention, wherein the compound of the invention is present in the composition in a diastereomeric excess of from 75% to 100%, 80% to 99.99%, 85% to 99.99%, 90% to 99.99%, 95% to 100%, 95% to 99.99%, 97% to 100%, or from 97% to 99.99%. For example, compounds of formula (I) include a tetrahydroquinoline central ring system with stereocenters at the ring carbons at positions 4 and 7 (see the numbering scheme depicted below). As a result, these compounds can exist as any of a variety of diastereomers (e.g., (4R, 7R), (4R, 7S), (4S, 7S), or (4S, 7R)). Substantially pure compositions are those compositions including one of the isomers in a diastereomeric excess. Substantially pure compositions can be prepared using standard resolution techniques and/or chiral synthetic schemes. The amount of each isomer present in the composition can be assessed using any of a variety of techniques known in the art, including optical rotation, column chromatography, and/or NMR spectroscopy. Substantially pure compositions can include non isomeric impurities (i.e., fillers, solvents, salts, and reaction side products) not relevant to the determination of diastereomeric excess.

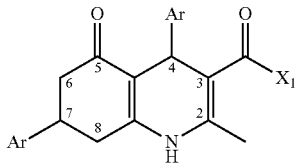

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-4}$ heteroalkyl, for example, includes from 1 to 3 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Exemplary cyclic groups include cyclopropyl, cyclobutyl, cyclopentyl, and cyclohexyl groups. The $C_{1-4}$ alkyl group may be substituted or unsubstituted. Exemplary substituents include alkoxy, aryloxy, sulfhydryl, alkylthio, arylthio, halide (e.g., $C_{1-4}$ haloalkyl, such as $CF_3$), hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; and cyclobutyl.

By "$C_{2-4}$ alkenyl" is meant a branched or unbranched hydrocarbon group containing one or more double bonds and having from 2 to 4 carbon atoms. A $C_{2-4}$ alkenyl. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl; allyl; 2-cyclopropyl-1-ethenyl; 1-propenyl; 1-butenyl; 2-butenyl; 3-butenyl; 2-methyl-1-propenyl; and 2-methyl-2-propenyl.

By "$C_{2-4}$ alkynyl" is meant a branched or unbranched hydrocarbon group containing one or more triple bonds and having from 2 to 4 carbon atoms. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{6-12}$ aryl" is meant an aromatic group having a ring system comprised of carbon atoms with conjugated $\pi$ electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{1-4}$ heteroalkyl" is meant a branched or unbranched alkyl, alkenyl, or alkynyl group having from 1 to 4 carbon atoms in addition to 1, 2, or 3 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{7-14}$ heteroalkaryl" is meant a heteroalkyl substituted by an aryl group (e.g., phenoxyethyl) having from 7 to 14 carbon atoms.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "hydroxyalkyl" is meant a chemical moiety with the formula —(R)—OH, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "alkoxy" is meant a chemical substituent of the formula —OR, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

Other features and advantages of the invention will be apparent from the following Detailed Description, the drawings, and the claims.

BRIEF DESCRIPTION OF THE DRAWINGS

FIG. 5A shows the changes in heart weight/body weight (HW/BW) ratio, an evidence of cardiac hypertrophy. FIG. 5B shows the changes in lung weight/BW (LW/BW) ratio, an indirect evidence for left heart failure. FIG. 5C shows the changes in ANF mRNA expression, biochemical evidence of cardiac hypertrophy and heart failure. Mice were infused with PE (30 mg/kg/day) via osmotic pump for 7 days. In FIGS. 5A-5C (i) Con=control group with the same amount of saline infusion by osmotic pump; (ii) Vehicle or VDRA (0.6 mg/kg) were injected 3x/week intraperitoneally; (iii) total volume injected=50 μL/animal/injection; (iv) *=p<0.05 vs Control; (v) **=p<0.05 vs Vehicle; and (vi) N=4.

DETAILED DESCRIPTION

Currently the calcemic effects of excess calcitriol (e.g., bone resorption, hypercalcemia, and calcification of soft tissue) limits its therapeutic use. This has resulted in a significant search for functional analogs of calcitriol that maintain potency but are safer as a result of a less intense calcemic response.

It is known that most of calcitriol's actions are mediated by a specific nuclear receptor the vitamin D receptor (VDR), which upon binding calcitriol undergoes a series of conformational events leading to the activation of the transcription of target genes through the association with the retinoid X nuclear receptor (RXR), coactivators of the p160 family (SRC-1), cointegrators that remodel chromatin (CBP), and mediator complexes that recruit RNA polymerase (DRIP/TRAP). Previously others have attempted to understand these processes through crystallographic studies of these complexes in which calcitriol or other agonist analogues (i.e., historically steroidal in nature) are bound to a modified human VDR ligand binding domain (hVDR Δ LBD).

Figure 1:
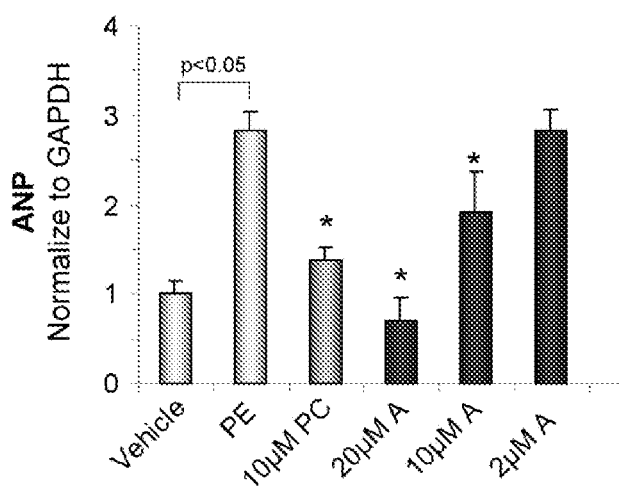
FIG. 1 is a graph depicting the trial natriuretic peptide (ANP) level response of cardiomyocytes to the specific hypertrophic stimulus phenylephrine (PE), with and without modulation by pretreatment with compound 10 (A) or paricalcitol (PC) (see Example 3 for details). Compound 10 exhibits a significant anti-hypertrophic effect in adult cardiomyocytes in vitro.

We have identified ~300 compounds of which ~200 have been evaluated in our high throughput screen of vitamin D receptor activity. Of these, 17 compounds, or 8.5% of the compounds evaluated, were found to have VDR agonistic activity at initial study concentrations of 50-100 μM. Second generation chemotype compounds, including compound 1, demonstrated the highest degree of agonistic activity in this assay, while compound 18 demonstrated modest agonist activity (see Tables 1 and 2 in Example 2). Using ligand-based scaffold expansion approaches we developed a structure-activity-relationship (SAR) series around compound 1, and through biochemical and cell-based readings identified compound 10 as the best in class. Compound 10 also showed a significant anti-hypertrophic effect in adult cardiomyocytes in cellulo (see FIG. 1 and Example 3).

Therapy

The compounds and compositions of the invention are useful for modulating the activity of vitamin D receptors, and for treating vitamin D receptor-mediated conditions.

For example, vitamin D receptor agonists have been shown to play a significant role in reducing parathyroid hormone levels (Hudson, J. Q. The Annals of Pharmacotherapy, 2006, 40, 1584-1593). As such, vitamin D receptor agonists are suitable for the treatment of conditions and disorders related to chronic kidney disease (conditional upon the deleterious effects associated with hypercalcemia associated with certain agonists). Some vitamin D receptor agonists do not upregulate intestinal vitamin D receptors, thus limiting adverse calcemic and hyperphosphatemic effects and the associated side effects (Slatopolsky, E.; Finch, J.; Ritter, C.; Takahashi, F. American Journal of Kidney Disease, 1998, 4, S40-S47). Studies have indicated that vitamin D receptor agonist therapy reduces the progression of renal disease (Agarwal, R.; Acharya, M.; Tian, J.; Hippensteel, R. L.; Melnick, J. Z.; Qiu, P.; Williams, L.; Bathle, D. Kidney International, 2005, 68, 2823-2828 and Schwarz, U.; Amann, K.; Orth, S. R.; Simonaviciene, A.; Wessels, S.; Ritz, E. Kidney International, 1998, 53, 1696-1705). Accordingly, the compounds of the invention can be used to reduce parathyroid hormone levels and treat kidney disease.

Vitamin D receptor agonists have been shown to be useful for skeletal and mineral homeostasis. These receptor agonists are important for intestinal calcium absorption and subsequent anabolic activity on bone (Hendy, G. N.; Hruska, K. A.; Methew, S.; Goltzman, D. Kidney International, 2006, 69, 218-223). Certain agonists have shown the potential to selectively treat bone disorders with a lessened effect on parathyroid hormone suppression. (Shevde, N. K.; Plum, L. A.; Clagett-Dame, M.; Yamamoto, H.; Pike, J. W.;

DeLuca, H. F. Proc. Natl. Acad. Sci. U.S.A. 2002, 99, 13487-13491; Uchiyama, Y.; Higuchi, Y.; Takeda, S.; Masaki, T.; Shira-Ishi, A.; Sato, K.; Kubodera, N.; Ikeda, K.; Ogata, E. Bone, 2002, 4, 582-588 and Shiraishi, A.; Higashi, S.; Ohkawa, H.; Kubodera, N.; Hirasawa, T.; Ezawa, I.; Ikeda, K.; Ogata, E. Calcified Tissue International, 1999, 65, 311-316). Accordingly, the compounds of the invention can be used to treat bone disorders.

Vitamin D receptor agonists are known to affect the circulatory system. The vitamin D receptor system plays an important role in maintaining antithrombotic homeostasis (Aihara, K.; Azuma, H.; Akaike, M.; Ikeda, Y.; Yamashita, M.; Sudo, T.; Hayashi, H.; Yamada, Y.; Endoh, F.; Fujimura, M.; Yoshida, T.; Yamaguchi, H.; Hashizume, S.; Kato, M.; Yoshimura, K.; Yamamoto, Y.; Kato, S.; Matsumoto, T. J. Biol. Chem., 2004, 279, 35798-35802). Vitamin D receptor agonists have been show to alter the expression and activity of proteins important for coagulation such as thrombomodulin, tissue factor, and plasminogen activator inhibitor 1 offering potential treatment in atherosclerotic diseases (Beer, T. M.; Venner, P. M.; Ryan, C. W.; Petrylak, D. P.; Chatta, G.; Ruether, J. D.; Chi, K. N.; Curd, J. G.; DeLoughery, T. G. British Journal of Haematology, 2006, 135, 392-394 and Ohsawa, M.; Koyama, T.; Yamamoto, K.; Hirosawa, S.; Kamei, S.; Kamiyama, R. Circulation, 2000, 102, 2867-2872). The renin-angiotensin II system is central in the regulation of blood pressure and elevated renin levels lead to hypertension, and cardiac hypertrophy. Vitamin D receptor agonists directly suppress renin gene transcription in a vitamin D receptor-dependent mechanism offering a control mechanism for this system (Li, Y. C.; Qiao, G.; Uskokovic, M.; Xiang, W.; Zheng, W.; Kong, J. Journal of Steroid Biochemistry & Molecular Biology, 2004, 89-90, 397-392). Patients with chronic kidney disease receiving maintenance hemodialysis often suffer cardiovascular complications of which ischemic heart disease as a result of left ventricular hypertrophy is the most prominent. Hyperparathyroidism is a contributor and even partial control with a vitamin D receptor agonist results in regression of myocardial hypertrophy without changes in other hemodynamic parameters (Park, C. W.; Oh, Y. S.; Shin, Y. S.; Kim, C.-M.; Kim, Y.-S.; Kim, S. Y.; Choi, E. J.; Chang, Y. S.; Bang, B. K. American Journal of Kidney Diseases, 1999, 33, 73-81). Accordingly, the compounds of the invention can be used to treat atherosclerosis, hypertension, ischemic heart disease, and cardiac hypertrophy.

Vitamin D receptor agonists are known to affect the immune system, modulating T cell responses. Currently vitamin D receptor agonists are used topically to treat psoriasis. Animal models show that vitamin D receptor agonists can be beneficial in the treatment of arthritis, autoimmune diabetes, experimental allergic encephalomyelitis, inflammatory bowel disease, and systemic lupus erythematosus, suggesting the expansion of therapeutic utility in humans (Adorini, L. Cellular Immunology, 2005, 233, 115-124). Accordingly, the compounds of the invention can be used to treat disorders of the immune system, such as nondermal inflammatory disorders (e.g., musculoskeletal disorders, such as gout, arthritis, osteoarthritis, or rheumatoid arthritis; inflammatory bowel disease, such as Crohn's disease, ulcerative colitis, ileitis, ileocolitis, collagenous colitis, lymphocytic colitis, ischaemic colitis, diversion colitis, Behçet's syndrome, indeterminate colitis, Crohn's colitis, Crohn's enteritis, Crohn's terminal ileitis, Crohn's entero-colitis, or ileo-colitis; inflammatory respiratory conditions, such as asthma, chronic obstructive pulmonary disease, bronchitis, rhinitis, sinusitis, or rhinosinusitis; inflammatory ocular conditions, such as uveitis, anterior uveitis, intermediate uveitis, posterior uveitis, panuveitis, vernal keratoconjunctivitis, atopic keratoconjunctivitis, iritis, or giant papillary conjunctivitis; nonproliferative dermal inflammatory disorders (e.g., acne, erythema multiforme, rash, or rosacea); and allergic reactions (e.g., asthma, graft vs host disease, contact dermatitis, urticaria, or allergic rhinitis).

A number of signaling pathways involved with cancer are affected by vitamin D receptor agonists, which can produce antiproliferative, anti-angiogenic, and pro-differentiation effects in a broad range of cancers mediated through both genomic and non-genomic mechanisms (Deeb, K. K.; Trump, D. L.; Johnson, C. S, Nature Reviews Cancer, 2007, 7, 684-700). The role of vitamin D metabolism seems to be important in the regulation of cell proliferation in the prostate (Lou, Y.-R.; Qiao, S.; Talonpoika, R.; Syvala, H.; Tuohimaa, P. Journal of Steroid Biochemistry and Molecular Biology, 2004, 92, 317-3250). There is an association of suppression of the autocrine growth factors IL-6 and IL-8 by vitamin D receptor agonists and the development of Kaposi sarcoma (Masood, R.; Nagpal, S.; Zheng, T.; Cai, J.; Tulpule, A.; Smith, D. L.; Gill, P. S. Blood, 2000, 96, 3188-3194). Vitamin D analogs exert a differentiating effect on leukemia cells (James, S. Y.; Williams, M. A.; Newland, A. C.; Colston, K. W. Gen. Pharmac., 1999, 32, 143-154). Accordingly, the compounds of the invention can be used to treat cancer and other conditions characterized by excessive cellular proliferation (e.g., cancers of the colon, prostate, breast, leukemia and Kaposi sarcoma; psoriasis, and hemangiomas, among others).

Compounds

Compounds of the invention include compounds of formula (I).

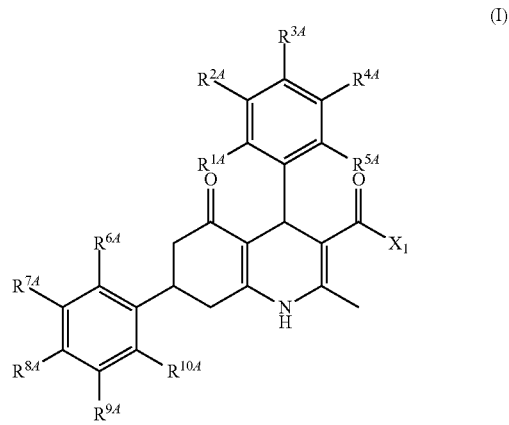

(I)

In formula (I) each of $R^{1A}$, $R^{2A}$, $R^{3A}$, $R^{4A}$, $R^{5A}$, $R^{6A}$, $R^{7A}$, $R^{8A}$, $R^{9A}$, and $R^{10A}$ is, independently, selected from H, halide, nitro, $CF_3$, OH, $OR^{11A}$, $C_{1-4}$ alkyl, $C_{1-4}$ heteroalkyl, $C_{2-4}$ alkenyl, and $C_{2-4}$ alkynyl; $X_1$ is $NHR^{12A}$, $OR^{12A}$, or $SR^{12A}$; $R^{11A}$ is selected from $C_{1-4}$ alkyl, $C_{2-4}$ alkenyl, and $C_{2-4}$ alkynyl; and $R^{12A}$ is selected from $C_{1-6}$ alkyl, $C_{1-6}$ heteroalkyl, $C_{2-6}$ alkenyl, $C_{2-6}$ alkynyl, $C_{6-12}$ alkaryl, and $C_{6-12}$ heteroalkaryl. Compounds of formula (I) include those compounds listed in Table 1.

Compounds of formula (I) can by prepared by condensation of an aryl substituted 1,3 cyclohexandione with a β-keto ester, ammonium acetate, and aromatic aldehyde via a multicomponent Hantzsch reaction (see Scheme 1).

Scheme 1

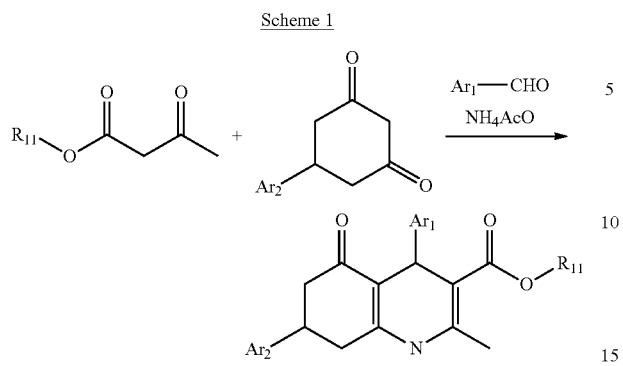

For exemplary reaction conditions, see Wang et al., Tetrahedron 61:1539 (2005); Zhang et al., ARKIVOC 2007 (xiii) 79; and Karade et al., Letters in Organic Chemistry 4:16 (2007). The corresponding thioester and amide derivatives can be prepared by hydrolysis of the ester product of Scheme 1, followed by activation of the resulting acid, and reaction with the desired amine or thiol.

Utilizing the Hantzsch reaction synthetic approach can result in a racemic mixture of isomers of formula (I) (shown below).

(4R,7R)

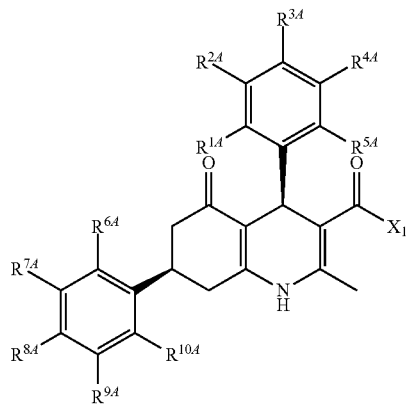

(4R, 7S)

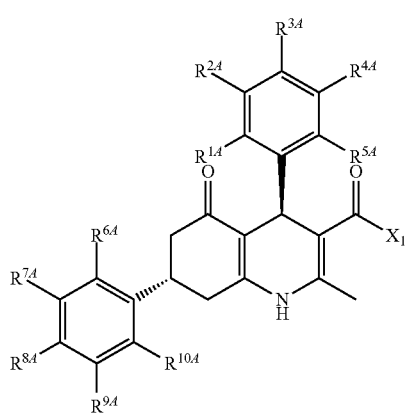

(4S,7R)

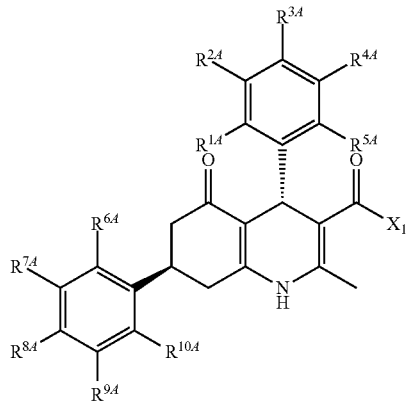

(4S, 7S)

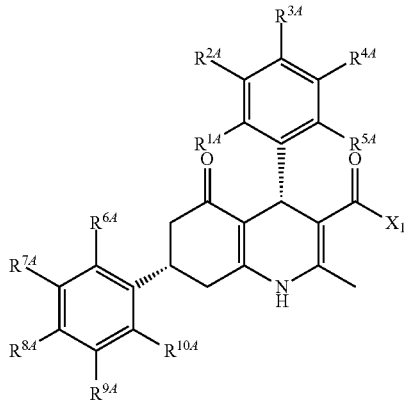

Substantially pure diastereomers can be prepared using a variety of techniques, including: (i) using chiral aryl substituted 1,3 cyclohexandione as a starting material to control the stereochemistry at position 7 in the compound of formula (I); (ii) separating mixtures of diastereomers by crystallization (e.g., cocrystallization with chiral acids or bases); (iii) separating mixtures of diastereomers by chromatography (i.e., optionally using a chiral mobile phase additive and/or a chiral stationary phase); and (iv) synthesizing a derivative including an easily removable chiral auxiliary to facilitate the isolation of a substantially pure diastereomer (i.e., once the desired diastereomer is isolated, the chiral auxiliary is removed).

Compounds of the invention include compounds of formula (II).

(II)

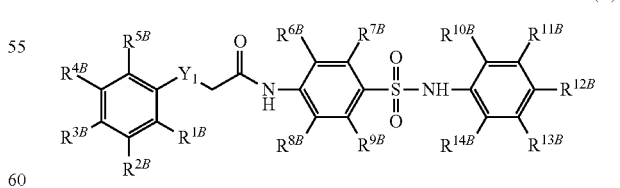

In formula (II) each of $R^{1B}$, $R^{2B}$, $R^{3B}$, $R^{4B}$, $R^{5B}$, $R^{6B}$, $R^{7B}$, RB, $R^{9B}$, $R^{10B}$, $R^{11B}$, $R^{12B}$, $R^{13B}$, and $R^{14B}$ is, independently, selected from H, halide, nitro, OH, $OR^{15B}$, $C_{1-4}$ haloalkyl, alkyl, $C_{1-4}$ alkyl, $C_{1-4}$ heteroalkyl, $C_{2-4}$ alkenyl, and $C_{2-4}$ alkynyl; $Y_1$ is O or S; and $R^{15B}$ is selected from $C_{1-4}$ alkyl, $C_{2-4}$ alkenyl, and $C_{2-4}$ alkynyl.

Compounds of formula (II) can by prepared in stepwise fashion, one step being a sulfonamide coupling, and second being a carboxamide coupling (see Scheme 2). In Scheme 2, the use of protecting groups is indicated in a structure by the letter P, where P may be any suitable protecting group listed below.

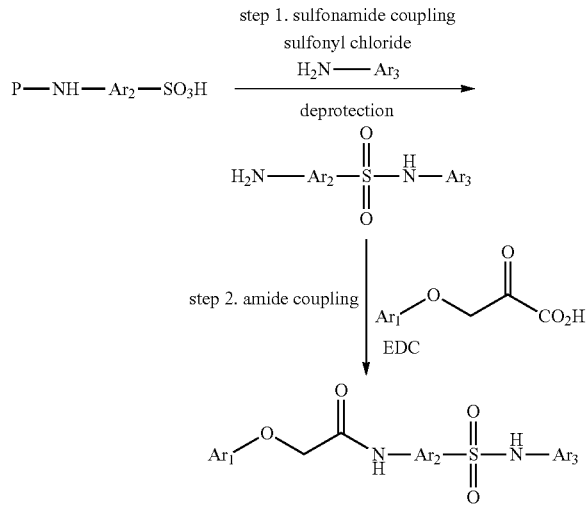

The synthesis of the compounds of the invention may involve selective protection and deprotection of alcohols, amines, sulfhydryls and carboxylic acid functional groups in one or more reactants. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in "T. W. Green and P. G. M. Wuts: Protective Groups in Organic Synthesis" ($2^{nd}$ ed., 1991, John Wiley & Sons) and "P. J. Kocienski: Protecting Groups" (1994 Georg Thieme Verlag); each of which is hereby incorporated by reference.

Formulation and Administration

Compounds of the present invention may be administered by any appropriate route for treatment or prevention of vitamin D receptor-mediated conditions. These may be administered to humans, domestic pets, livestock, or other animals with a pharmaceutically acceptable diluent, carrier, or excipient, optionally in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc and iron, among others.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Many strategies can be pursued to obtain targeted delivery of the compound to a particular cell type or tissue. For example, the compounds of the invention can be covalently attached to a targeting moiety (e.g., an antibody), via a biodegradable linker (i.e., administered as a targeted prodrug conjugate linked to the targeting moiety via one or more hydrolyzable bonds, such as an ester, thioester, or carbamate bond). The targeting moiety can be a peptide or peptidomimetic (e.g., bombesin-like peptides, somatostatin-like peptide, RGD peptides, or EPPT1 peptide), low molecular weight ligand (e.g., methotrexate, trimetrexate, or folate), protein (e.g., an antibody or fragment thereof, such as rituximab, cetuximab, trastuzumab, bevacizumab, and abciximab), polymer (e.g., a polymer including a polypeptide, polysaccharide, or polyethyleneglycol), solid support, anticancer agent (e.g., alkylating agents, folic acid antagonists, pyrimidine antagonists, purine antagonists, antimitotic agents, DNA topomerase II inhibitors, DNA topomerase I inhibitors, taxanes, DNA intercalators, aromatase inhibitors, 5-alpha-reductase inhibitors, estrogen inhibitors, androgen inhibitors, gonadotropin releasing hormone agonists, retinoic acid derivatives, or hypoxia selective cytotoxins), or anti-inflammatory agent (e.g., non steroidal anti-inflammatory drugs, COX-2 inhibitors, anti-inflammatory biologics, and corticosteroids). The targeting moiety can be selected to alter receptor binding, biodistribution, pharmacokinetics, oral bioavailability, protein binding, and/or solubility, as desired.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided in unit dosage form as chewable tablets, tablets, caplets, or capsules (i.e., as hard gelatin capsules wherein the active ingredient is mixed with an inert solid diluent, or as soft gelatin capsules wherein the active ingredient is mixed with water or an oil medium).

The compound of the invention can be administered to human subjects in therapeutically effective amounts. Typical dose ranges are from about 0.0004 µg/kg to about 0.5 µg/kg of body weight per day. The preferred dosage of drug to be administered is likely to depend on such variables as the type and extent of the disorder, the overall health status of the particular subject, the specific compound being administered, the formulation of the compound excipients, and its route of administration. Standard clinical trials maybe used to optimize the dose and dosing frequency for any particular compound. For example, the compounds of the invention can be formulated in unit dosage form (i.e., a capsule or tablet) containing from 0.025 µg to 50 µg of the compound, or a salt thereof. The effective daily dose can be divided into multiple doses for purposes of administration. Consequently, single dose compositions may contain such amounts or submultiples thereof to make up the daily dose.

The compounds of the invention can be formulated for topical administration. For example, the compounds can be administered topically as a skin cream, a facial cream; a cleanser, a toner, a day cream, a night cream, a day lotion, an eye cream, a facial mask (e.g., firming, moisturizing, purifying, deep-cleansing), an anti-aging cream, an anti-wrinkle cream, an anti-puffiness product, a cold weather cream, a foot cream; a facial scrub; a hand cream; hair care products; beauty treatment products; a perfume; a bath and body product; a suncare product; or combinations thereof. The compounds can be administered topically as a hair care product, such as a shampoo, a conditioner, a re-conditioner, a mousse, a gel, a hair spray, a hair mascara, a hot oil treatment product, a dye, a deep conditioning treatment product, a coloring product, a hair-repair product, a permanent wave product, or combinations of thereof. The compounds can be administered topically as a bath or body product, such as a shower gel, including an exfoliating shower gel, a foaming bath product (e.g., gel, soap or lotion), a milk bath, a body wash, a soap (including liquid and bar soap), a cleanser, including a gel cleanser, a liquid cleanser, a cleansing bar, a body lotion, a body spray, mist or gel, an essential lotion, a slimming lotion, bath effervescent tablets, a hand and nail cream, a bath/shower gel, a shower cream, a cellulite smoothing product, a deodorant, a dusting powder, an antiperspirant, a depilatory cream, or a shaving product (e.g., a shaving cream, a gel, a foams and an after-shave, after-shave moisturizer). Any conventional pharmacologically and cosmetically acceptable vehicles may be used. For example, the compounds may also be administered in liposomal formulations that allow compounds to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. No. 4,877,805 and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil. The formulations can include various conventional colorants, fragrances, thickeners (e.g., xanthan gum), preservatives, humectants, emollients (e.g., hydrocarbon oils, waxes, or silicones), demulcents, solubilizing excipients, dispersants, penetration enhancers, plasticizing agents, preservatives, stabilizers, demulsifiers, wetting agents, sunscreens, emulsifiers, moisturizers, astringents, deodorants, and the like can be added to provide additional benefits and improve the feel and/or appearance of the topical preparation. The formulations are typically used for the prophylaxis and/or treatment of the skin in the context of dermatological treatment and/or for promoting hair growth or reducing hair loss. Accordingly, the formulations of the invention are desirably formulated as a cream, lotion, ointment, salve, soap or body wash, shampoo, or a mask. However, the formulations can also be employed in make-up products, such as bases, blushes, lipsticks, and eye shadows, among others. They preferably include 0.00005% by weight to 5% by weight, preferably 0.0001% by weight to 2% by weight, of a compound of the invention. The application regimen (i.e., daily, weekly, etc.) for the topical formulation will primarily depend upon the longevity (e.g., metabolism, half-life in the skin) of the agents and the skin condition to be treated. For topical administration, the regimen may also be affected by bathing, perspiration, and the extent of sunlight exposure. Usually, the formulation will be administered at least once daily. Typically, about 1 to 50 mg of formulation will be applied per cm2 of skin.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

In Silico Pharmacophore Elucidation

Computer-Aided Molecular Modeling.

All molecular modeling operations were performed in the Maestro (Schrödinger Inc.) and MOE (CCG) modeling packages running on Dell Precision 690 workstation with 4 CPUs, 10 GB memory and RHE Linux 5 OS. The chemical libraries employed in the virtual screens included Chembridge, Asinex, NCI and ZINC databases which were filtered for the Lipinski rule of 5 for drug-likeness. The structures were prepared using Ligprep program, which converted 2D chemical files to protonated 3D structures that were energetically optimized. The program Epik, which partners the proven reliability of the Hammett and Taft methods with powerful tautomerization tools, to identify possible ionization and tautomer states at physiological pH (7.0±2.0), along with generating ring conformers and stereoisomers with default settings was used on all 4 million unique structures generated. The ionization state penalties for each protomer state were calculated and stored for use in calculations of the docking score.

Pharmacophore Elucidation.

Pharmacophore hypotheses were generated using 13 highly potent analogs of 1,25-D, which were energy optimized in the binding pocket of an optimized crystal structure (PDB code: 1DB1). This receptor-aligned set of structures was subjected to pharmacophore elucidation protocol involving the implementation of the program, Phase program for calculation of sites (features), followed by identification of common features and hypotheses scoring which is an additive score comprised of three components: site, vector and alignment scores. Hypothesis generation and evaluation resulted in the identification of a single hypothesis that survived validation when multiple conformations of ligands (against receptor-bound single conformation) were used for alignment. One of the five-feature models (DDHHH.30) that survived this scoring criteria was chosen for database screening; as a coincidence 1,25-D appeared as a reference structure for alignment and scoring of this pharmacophore, supporting that features of all other molecules are compared with 1,25-D.

High-Throughput Docking

Hits from pharmacophore screens (fitness score ≥1.0) were subjected to structure-based docking evaluations using multiple X-ray crystal structures of human VDR-LBD in complex with: 1,25-D (PDB code: 1DB1), 2α-(3-hydroxy-1-propyl)-1,25-D (PDB code: 2HB7) and the super agonist AMCR277B (a cyclic side-chain analog of 1,25-D; PDB code: 3CS6), nominally resolved at 1.5-1.8 Å range. The structures were prepared using the protein preparation wizard utility in Maestro GUI, in which ions and water molecules were deleted and all hydrogen atoms added. The ionization states of bound ligand and charged side chains of the protein were calculated followed by optimization of hydrogen bond network and constrained (impref) energy minimization of only hydrogen atoms, up to RMSD of 0.3 Å. For each PDB conformation used in this ensemble docking protocol the receptor grids, which represent shape and several properties of receptor including charges and electrostatics, were generated for active sites with native ligand as the center. The docking was performed in standard precision (SP) scoring function, followed by more rigorous evaluation of hits with SP scores ≥−8.0 kcal/mol using extra precision (XP) docking simulation, with consideration to ionization state penalty in docking score calculation.

Post-Docking Analysis and Consensus Ranking.

After XP docking, hits with docking score better than −8.0 kcal/mol were considered for post-docking analysis. The top scoring pose of each molecule was given a unique rank based on the docking score in each PDB conformation. Similar ranking was assigned to these molecules based on pharmacophore fitness scores. These four rankings, three for docking in 3 PDB conformations and one for fitness score, were taken into account for consensus ranking of top-scored molecules.

Results of the Computer-Aided Molecular Design:

Advances in scientific computing have opened new avenues to identifying hit/lead molecules modulating a specific target under study. In recent years, virtual or in silico screens of small-molecule chemical libraries have proven to provide accelerated opportunities to rationally filter large compound repositories in a search for ligands comprised of unique molecular descriptors that have been ascribed important mechanism of action (MOA) properties. We identified several non-steroidal agonists and antagonists of human VDR using an in silico flow scheme, which combined ligand-based pharmacophore screens with ensemble structure-based docking studies—a process that leverages the strengths of each approach and helps mitigate limitations of each approach. In order to achieve scaffold hopping and identify novel non-steroidal compounds, we biased our screening towards the chemical features of known agonists, with the goal of identifying compounds devoid of the often demonstrable, but severely limiting hypercalcemia activity, followed by rigorous structure-based evaluation of hits in an induced fit-ensemble docking approach using multiple structures and models of the VDR-LBD. Briefly, a pharmacophore query was created by incorporating the common features of highly potent VDR agonists, edited and energy optimized within the LBD binding pocket by ensuring maximum ligand efficiencies were obtained for identified hit compounds. The selected five-feature hypothesis enclosed 3 hydrophobic features (with highest energetic contribution to binding affinity based on XP descriptors) and 2 hydrogen bond donors, which participate in hydrogen bonding with R274, S232, Y143, S278 residues. Screening of approximately 4 million unique compounds made available through Chembridge, Asinex, NCI and ZINC databases, considering multiple ionization/tautomer states and conformations and fitting at least 4 features, resulted in 10,000 unique hits with acceptable fitness scores (>1.0). These hits were then subjected to cross-docking evaluations in three VDR-LBD conformations to account for possible induction in the receptor flexibility after ligand binding.

The ligand binding domain (LBD) of VDR is comprised of 12 helices and several f-turns, eleven of these helices form ligand binding pocket while last helix, H12 forms a flexible lid that many believe functions by providing a capping mechanism that covers and/or occludes the entrance to the pocket and thus exit of bound ligands. Binding of 1,25-D to VDR-LBD causes conformational change in the VDR which shifts the equilibrium towards active conformation to form activation function 2 (AF2), a hydrophobic cleft formed by three helices and a short C-terminal amphipathic α-helix H12. It serves as binding surface for coactivators which binds as a heterodimer with the retinoid X receptor to vitamin D response elements (VDREs). Recruitment of coactivator proteins to this heterodimer is critical for the transactivation. In contrast, antagonist ligand shifts the equilibrium of receptor conformations to inactive conformation that interacts with corepressor (instead of coactivators) and as a result transactivation remains silent. The closed (active) conformation of VDR is represented by agonist-bound structures. To account for this conformational change as a function of ligand structure, we attempted to incorporate limited receptor flexibility during docking evaluation of pharmacophore filtered molecules. There are several approaches to derive the multiple conformations of a target receptor (molecular dynamics simulations), however we have decided to rely on experimentally calculated X-ray crystal structures that represent a specific snapshot of the receptor in complex with a requisite ligand. The selection of crystal structures used for our ensemble docking approach was based on the uniqueness of the receptor-ligand complex in the co-crystal structure including: PDB codes—1DB1, 2HB7 and 3CS6. A structure-based virtual screen was then performed, which involved two rounds of docking into the conformational ensemble detailed above. In the first round of ensemble docking, 10,000 hits were evaluated and ranked using a simplified standard precision (SP) scoring function. In the second round of docking, the hits with SP score greater than −8.0 were subjected to a rigorous conformational evaluation using the extra precision (XP) scoring metrics, a scoring and ranking functionality that reduce the number of false positives in virtual screening experiments that improves active enrichment as many have documented. Top ranked unique hits in each PDB conformation were analyzed to evaluate various hypotheses to identify which individual or combination of PDB conformation is capable of enriching the ranking of hits.

EXAMPLE 2

High Throughput Binding Assays

High throughput assay validation of the top ranked unique molecules from each of three PDB conformations on the basis of docking score (glide score+ionization state penalty). From this priority list 200 of the best ranked molecules, following ADMET evaluation, were purchased and subjected to binding assays. The compounds of formula (I) were obtained and tested as a mixture of diastereomers.

To determine which compounds identified by virtual screens are actually capable of regulating the transcriptional profile of VDR, we performed GeneBLAzer® Cell-Based VDR Assay (kit was bought from Invitrogen and assay performed as per instructions). Upon binding of a VDR agonist to the targeting construct (GAL4-DBD/VDR-LBD) fusion protein engineered in a HEK293T cell line containing 7XUAS-bla, a transcriptional cascade is initiated that produces β-lactamase (BLA). In the presence of the BLA LiveBLAzer™ substrate, cells expressing BLA will fluoresce blue (460 nm), while those not expressing BLA will fluoresce green (530 nm); higher 530/460 ratio indicating the activation of VDR, whereas in presence of calcitriol (potent agonist) diminishing of this ratio indicates an antagonist behavor of the ligand. The agonist and antagonist abilities of CADD-selected compounds were determined in six-point concentration profile and compared with vehicle.

Materials:

GeneBLAzer® VDR-UAS-bla HEK 293T cells were purchased from Invitrogen (Cat# K1700). The cells were cultured in growth medium in a humidified (37° C./5% $CO_2$) incubator following the manufacture's instruction. Test compounds (ChemBridge, San Diego, Calif.) and Calcitriol (1α,25-Dihydroxyvitamin D3, Sigma) were dissolved in 100% DMSO(Sigma) at 1000-fold stock concentration and stored at −20° C., which were diluted in assay medium immediately prior to use. LiverBLAzer-FRET B/G loading kit was purchased from Invitrogen.

Methods:

The GeneBLAzer® VDR-UAS-bla HEK 293T cell-based assay was used to screen 200 compounds for activity at the vitamin D receptor. The assay was run in triplicate following the manufacture's instruction. Briefly, $2 \times 10^4$ cells in 32 μl assay medium were added to each well of a 384-well black-wall assay plate (Corning Incorporated, Cat#3712). To each well was added 8 al of compound solution diluted in assay medium, the cells were incubated in a humidified (37° C./5% $CO_2$) incubator for 5 hours. The cell-free wells (containing 32 μl assay medium only) and unstimulated cell wells were treated in parallel with the same concentration of DMSO in assay medium, which were used as background controls and blank controls, respectively. Calcitriol was used as a positive control. To each well was added 8 μl of LiverBLAzer-FRET B/G substrate mixture. The plate was covered with plate sealer and incubated at room temperature for 2 hours in the dark. Fluorescence emission was measured on SpectraMax plate reader at 460 nm and 530 nm with excitation set to 409 nm. After subtraction of background, the average value at 460 nm was divided by the average value at 530 nm to obtain the 460/530 ratio.

Binding Assay Results:

The cell-based GeneBlazer assay confirmed that 14 hits were capable of activating (agonizing) the VDR at micromolar and submicromolar concentrations. 15 compounds possessed demonstrable antagonism (low micromolar concentrations) in presence of 1,25-D as illustrated in inhibition assays involving the VDR. The chemical scaffold of one of the best agonist compound 1 was explored further to evaluate a limited structure-activity relationship (SAR) by performing substructure screens following re-evaluation of hits through the screening protocol described above; out of 25 compounds purchased and tested, 14 showed equal or better agonist activity in a dose-dependent manner at concentrations as low as 5 μM concentrations. Compound 10 was selected for testing in a mouse model of cardiac hypertrophy. The structures of the hits identified through the in silico screens and functionally validated using cell based screens are provided in Tables 1 and 2.

TABLE 1

Structure and activity of members of compounds of formula (I).

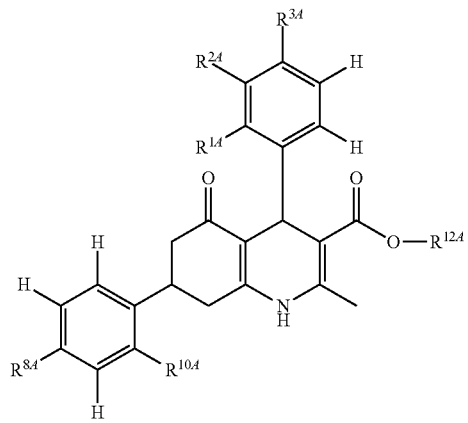

| # | Activity | $R^{12A}$ | $R^{1A}$ | $R^{2A}$ | $R^{3A}$ | $R^{8A}$ | $R^{10A}$ |
|---|---|---|---|---|---|---|---|
| 1 | Agonist | CH2—CH2—S—CH2—CH3 | — | — | — | — | — |
| 2 | Agonist | CH2—CH3 | — | — | F | Cl | — |
| 3 | Agonist | CH2—CH2—O—Ph | — | OH | OCH3 | — | — |
| 4 | Antagonist | CH2—CH3 | — | OH | — | OCH3 | — |
| 5 | Agonist | CH2—CH2—O—Ph | — | — | CH2—CH3 | OCH3 | — |
| 6 | Agonist | CH2—CH2—S—CH2—CH3 | F | — | — | — | OCH3 |
| 7 | Agonist | CH2—CH2—S—CH2—CH3 | — | OCH2—CH3 | OH | OCH3 | — |
| 8 | Agonist | CH2—CH2—O—CH3 | — | — | Br | Cl | — |
| 9 | Antagonist | CH2—CH3 | — | — | OH | OCH3 | — |
| 10 | Agonist | CH2—CH2—S—CH2—CH3 | — | OCH3 | — | Cl | — |
| 11 | Agonist | CH2—CH2—S—CH2—CH3 | F | — | — | Cl | — |
| 12 | Agonist | CH2—CH2—O—Ph | — | — | — | OCH3 | — |
| 13 | Agonist | CH2—CH2—S—CH2—CH3 | F | — | — | OCH3 | — |
| 14 | Agonist | CH2—CH2—O—CH3 | — | — | CH3 | Cl | — |
| 15 | Agonist | CH2—CH2—S—CH2—CH3 | OCH3 | — | — | Cl | — |
| 16 | Agonist | CH2—CH2—O—CH2—CH3 | — | — | F | Cl | — |
| 17 | Agonist | CH2—CH2—S—CH2—CH3 | OCH3 | — | — | OCH3 | — |

"—" = H atom.

Compounds that can be used in the methods and compositions of the invention include any of compounds 1-17, each in any of their available diastereomeric configurations (e.g., (4R,7R), (4R,7S), (4S,7S), or (4S,7R)).

Of the 200 compounds assayed, 14 were found to be agonists at 500 µM (5 compounds showed considerable activation at 100 µM), whereas 15 compounds exhibited antagonism by inhibiting VDR activation at 50 µM. From the hit maturation (second generation) series derived on the basis of compound 1, several compounds were agonists at 50 µM, with 8 of these being as potent as the parent compound 1 but not necessarily superior (see Table 1).

TABLE 2

Structure and activity of members of compounds of formula (II).

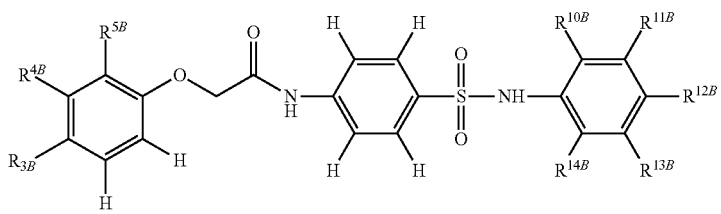

| # | Activity | $R^{3B}$ | $R^{4B}$ | $R^{5B}$ | $R^{10B}$ | $R^{11B}$ | $R^{12B}$ | $R^{13B}$ | $R^{14B}$ |
|---|---|---|---|---|---|---|---|---|---|
| 18 | Agonist | CH3 | — | — | CH3 | — | CH3 | — | CH3 |
| 19 | Agonist | Cl | — | — | CH3 | — | CH3 | — | CH3 |
| 20 | Agonist | — | — | CH3 | CH3 | — | CH3 | — | CH3 |
| 21 | Antagonist | C2H5 | — | — | — | CH3 | — | CH3 | — |
| 22 | Antagonist | Cl | — | Cl | CH3 | — | CH3 | — | CH3 |
| 23 | Antagonist | — | CH3 | — | — | — | CH3 | — | CH3 |
| 24 | Antagonist | — | — | CH3 | — | — | OCH3 | — | — |

"—" = H atom.

EXAMPLE 3

Functional Cell Culture Studies

Model of hypertrophy in adult cardiomyocyte in vitro:

We used adult rat cardiomyocytes (ARCMs) in these studies because heart failure is predominantly a disease of the adult heart. ARCM cultures were prepared from the hearts of female Sprague-Dawley rats by enzymatic dissociation using 0.3% collagenase. Each heart yields about $3\text{-}4 \times 10^6$ viable ventricular cardiomyocytes. Freshly isolated adult cardiomyocyte cultures contain >90% rod-shaped myocytes and less than 1% of the cells are non-myocytes. The cells were used within 24 hours of plating.

We examined how the response of cardiomyocytes to specific hypertrophic stimulus, phenylephrine (PE) is modulated by pretreatment with compound 10 as compared to known activated vitamin D analog, paricalcitol (PC). In this experiment, ARCM was pre-treated with vehicle, compound 10 (different doses) or paricalcitol (100 μM) for 24 hours. The cells were then exposed to PE (100 μM) or vehicle for 48 hours. After exposing the cells to hypertrophic stimulation for 48 hours, they were collected and analyzed for several well-established parameters of cardiac hypertrophy, such as tissue atrial natriuretic peptide (ANP) level. Compound 10 exhibited a significant anti-hypertrophic effect in adult cardiomyocytes in vitro (see FIG. 1).

EXAMPLE 4

Calcemic Effects

We performed short-term (24 hours) and long-term (7 days) in vivo experiments comparing the calcemic effect of compound 10 (aka VDRA) to an equivalent dose of calcitriol.

For this study, we used 1α-hydroxylase (1α-OH) knock out (KO) mice, which lack 1α-OH, an enzyme that converts 25(OH)VitD$_3$ to the hormonally active form, 1,25-dihydroxyvitamin D$_3$ (1,25(OH)$_2$VitD$_3$) or calcitriol. These mice are designed to have a low vitamin D level at baseline and are hypocalcemic.

For the short term experiment, we administered 0.6 μg/kg (therapeutic dose) and 3 μg/kg (supratherapeutic dose) of vehicle, calcitriol or compound 10, and then measured serum calcium level 24 hours after administration.

For the long-term experiment, we administered 0.6 μg/kg of vehicle, calcitriol or compound 10 for one week. We administered the drugs on Wednesday, Friday, and Monday, and measured serum calcium level on the following Tuesday.

Serum ionized calcium levels were measured using clinical grade iSTAT system (Abbott laboratories).

Results

Figure 2:
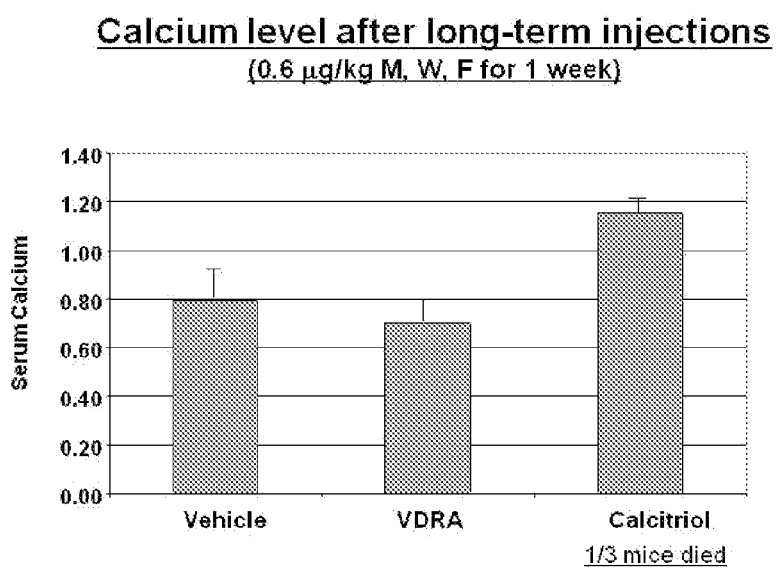
FIG. 2 is a graph depicting serum calcium levels in 1α-hydroxylase knock out mice following long term administration of vehicle, compound 10 (VDRA) or calcitriol (see Example 4 for details). We found that with long term use calcitriol produced about a 45% increase in serum calcium levels compared to the vehicle alone, while compound 10 did not produce any increase in calcium levels compared to the vehicle.
Figure 3:
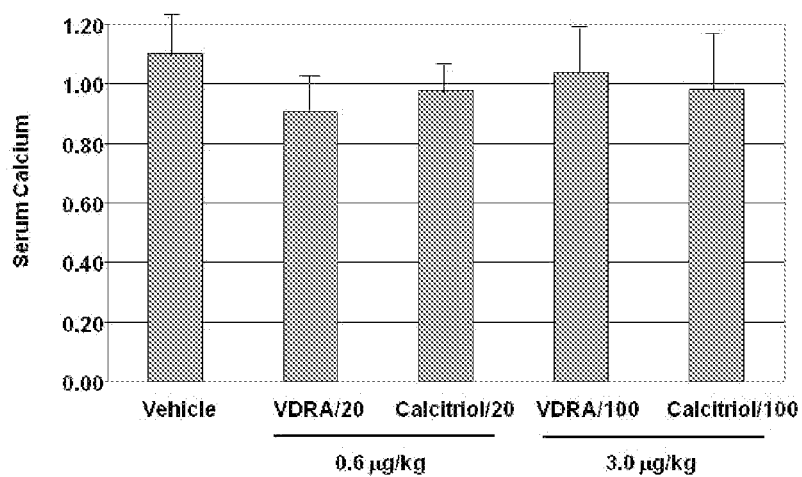
FIG. 3 is a graph depicting serum calcium levels in 1α-hydroxylase knock out mice 24 hours after administration of vehicle, compound 10 (VDRA) or calcitriol (see Example 4 for details). We found that calcitriol and compound 10 did not show any significant increase in calcium levels at both 0.60 and 3.0 μg/kg doses compared to the vehicle at this early time point.

In short term experiment, we found that calcitriol and compound 10 did not show significant increase in calcium level at both 0.60 and 3.0 μg/kg doses compared to the vehicle (see FIG. 3). However, in long term experiment, we found that calcitriol showed about 45% increase in serum calcium level compared to the vehicle (see FIG. 2). Compound 10, however, did not show any increase in calcium level compared to the vehicle. Thus, we conclude that compound 10 lacks the calcemic effects seen in calcitriol compared to the vehicle.

The compounds of the invention may be administered chronically to subjects in need without inducing hypercalcemia.

EXAMPLE 5

Inhibition of Hyperparathyroidism

We performed long-term (7 days) in vivo experiments comparing the parathyroid hormone (PTH) levels following administration of compound 10 (aka VDRA) to an equivalent dose of paricalcitol (PC), a VDR agonist used to treat secondary hyperparathyroidism.

For this study, we used 1α-hydroxylase (1α-OH) knock out (KO) mice, which lack 1α-OH, an enzyme that converts 25(OH)VitD$_3$ to the hormonally active form, 1,25-dihydroxyvitamin D$_3$ (1,25(OH)$_2$VitD$_3$). These mice are designed to have a low vitamin D level at baseline and are hypocalcemic.

We administered 0.6 μg/kg of compound 10 or paricalcitol three times a week (Mon, Wed, Fri) for three weeks. Serum PTH level was measured using a PTH (intact, mouse) ELISA immunoassay (Alpco, Salem, Mass.).

Results

Figure 4:
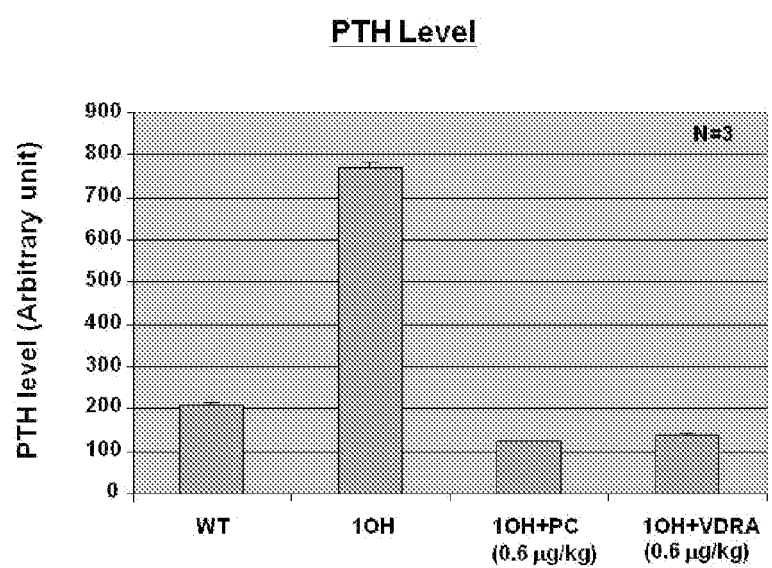
FIG. 4 is a graph depicting parathyroid hormone (PTH) levels in 1-hydroxylase knock out mice (1OH) following long term administration of vehicle, compound 10 (VDRA) or paricalcitol (PC) (see Example 5 for details). Both compound 10 and PC were given at 0.60 μg/kg. We found that the knock out mice (1OH) had significantly higher PTH levels compared to the wild type (WT) mice, and that both compound 10 and paricalcitol significantly reduced PTH levels in the knock out mice.

We found that 1α-OH KO mice (1OH) had significantly higher PTH levels compared to the WT mice (see FIG. 4). We also found that administration of both compound 10 and paricalcitol significantly reduced PTH levels in 1α-OH KO mice (see FIG. 4). Thus, we conclude that compound 10 inhibits hyperparathyroidism in animals that are vitamin D deficient.

The compounds of the invention can be useful for the treatment of hyperparathyroidism.

EXAMPLE 6

Inhibition of Cardiac Hypertrophy and Heart Failure by Compound 10 In Vivo

The anti-hypertrophic potential of compound 10 (aka VDRA) in phenylephrine (PE) induced cardiac hypertrophy in mice was evaluated in vivo. WT mice were infused with phenylephrine (PE) (30 mg/kg/day) via osmotic pump for 7 days. After 7 days, the mice were sacrificed, organ weighed, and hearts were obtained for mRNA processing. Vehicle or compound 10 (60 ng/kg) were injected 3×/week intraperitoneally (total volume injected=50 μL/animal/injection).

Figure 5:
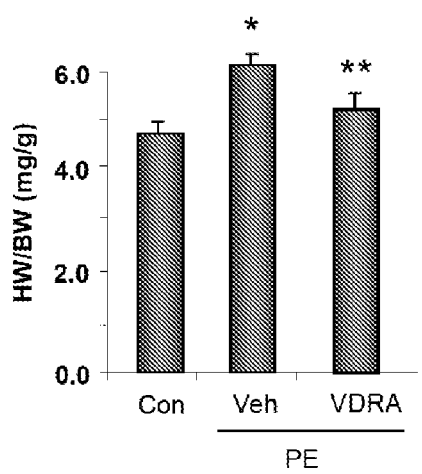
FIGS. 5A-5C are bar graphs depicting the anti-hypertrophic potential of compound 10 (aka VDRA) in phenylephrine (PE) induced cardiac hypertrophy in mice (see Example 6). Compound 10 demonstrates significant anti-hypertrophic effects in vivo.
Figure 5:
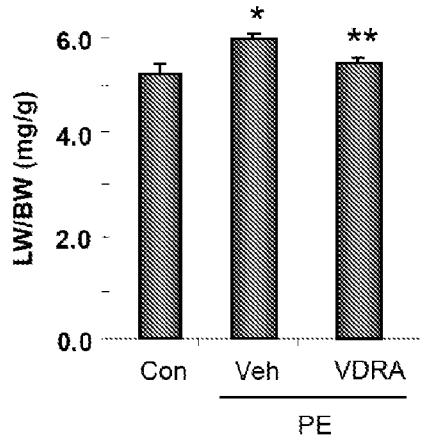
Figure 5:
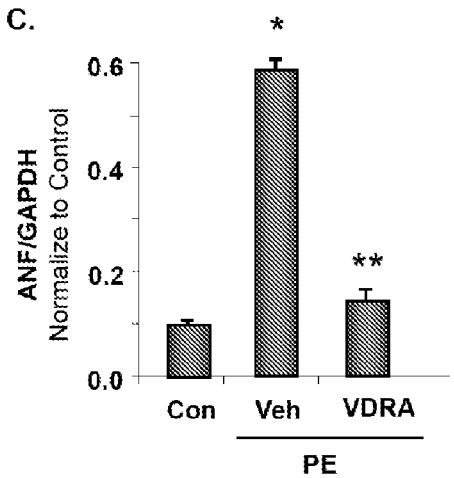

Infusion of PE over 7 days resulted in significant increase in heart weight/body weight (HW/BW) ratio, indication of cardiac hypertrophy, and increase in lung weight/BW (LW/BW) ratio, an indirect evidence for left heart failure (see FIGS. 5A and 5B). Administration of compound 10 effectively blocked PE-induced HW/BW and LW/BW ratios. In addition, PE also induced ANF (atrial natriuretic factor) activation in left ventricular tissue, which was effectively suppressed by administration of compound 10 (see FIG. 5C). From these data, we conclude that compound 10 could exert known biological effects of vitamin D such as prevention of cardiac hypertrophy, both in vitro and in vivo settings.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for treating a vitamin D receptor-mediated condition in a subject in need thereof, said method comprising administering to said subject the compound:

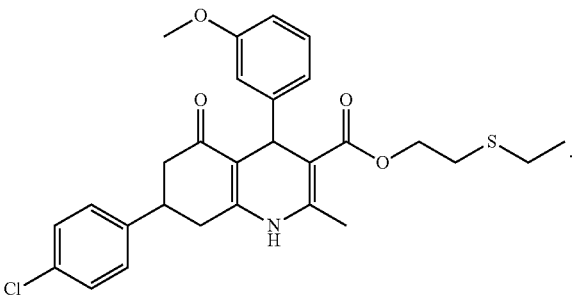 [SMILES: CCSCCOC(=O)C1=C(C)NC2=C(C(=O)CC(c3ccc(Cl)cc3)C2)C1c1cccc(OC)c1]

or a pharmaceutically acceptable salt thereof, in an amount sufficient to treat said condition, and wherein said condition is selected from cardiac hypertrophy and hyperparathyroidism.

2. The method of claim 1, wherein said vitamin D receptor-mediated condition is hyperparathyroidism.

3. The method of claim 1, wherein said vitamin D receptor-mediated condition is cardiac hypertrophy.

* * * * *